(12) United States Patent
Archer et al.

(10) Patent No.: US 9,487,465 B2
(45) Date of Patent: Nov. 8, 2016

(54) PROCESS FOR THE SEPARATION OF MONO- AND DI-CARBOXYLIC ACID COMPOUNDS

(71) Applicant: Rennovia, Inc., Menlo Park, CA (US)

(72) Inventors: Raymond Archer, San Jose, CA (US); Gary M. Diamond, Menlo Park, CA (US); Eric L. Dias, Belmont, CA (US); Vincent J. Murphy, San Jose, CA (US); Miroslav Petro, San Jose, CA (US); John D. Super, Houston, TX (US)

(73) Assignee: Rennovia Inc., Santa Clara, CA (US)

( * ) Notice: Subject to any disclaimer, the term of this patent is extended or adjusted under 35 U.S.C. 154(b) by 132 days.

(21) Appl. No.: 13/691,611

(22) Filed: Nov. 30, 2012

(65) Prior Publication Data

US 2013/0345473 A1 Dec. 26, 2013

Related U.S. Application Data

(60) Provisional application No. 61/570,624, filed on Dec. 14, 2011.

(51) Int. Cl.
| | |
|---|---|
| *C07C 51/47* | (2006.01) |
| *C07C 51/377* | (2006.01) |
| *B01D 15/36* | (2006.01) |
| *B01D 15/18* | (2006.01) |
| *B01D 15/16* | (2006.01) |

(52) U.S. Cl.
CPC ........... *C07C 51/377* (2013.01); *B01D 15/363* (2013.01); *C07C 51/47* (2013.01); *B01D 15/16* (2013.01); *B01D 15/185* (2013.01); *B01D 15/1821* (2013.01)

(58) Field of Classification Search
None
See application file for complete search history.

(56) References Cited

U.S. PATENT DOCUMENTS

| | | | |
|---|---|---|---|
| 2,664,441 A | * | 12/1953 | Owens et al. ................. 548/534 |
| 4,400,468 A | | 8/1983 | Faber |
| 5,487,987 A | | 1/1996 | Frost et al. |
| 6,284,904 B1 | | 9/2001 | Ponnampalam |

(Continued)

FOREIGN PATENT DOCUMENTS

| | | | |
|---|---|---|---|
| EP | 2345632 | * | 7/2011 |
| EP | 2345632 A1 | | 7/2011 |
| WO | 2008/019468 A1 | | 2/2008 |

OTHER PUBLICATIONS

Ericsson et al., Journal of Chromatography, 134 (1977) 337-342.*

(Continued)

*Primary Examiner* — Karl J Puttlitz
(74) *Attorney, Agent, or Firm* — Senniger Powers LLP

(57) ABSTRACT

The present disclosure relates to processes for the separation of at least one di-carboxylic acid compound and/or at least one mono-carboxylic acid compound from a mixture. The separation processes involve contacting the mixture with an ion exchange medium to cause at least one of the mono- and/or di-carboxylic acid compounds to be retained by the medium, eluting at least one of the mono-carboxylic acid compound or the di-carboxylic acid compound using an eluent to form an eluate, wherein the eluate is enriched in at least one of the mono-carboxylic acid compound or di-carboxylic acid relative to the concentration of such eluted acid in the mixture having contacted the medium and wherein the eluent comprises an organic acid. The process has particular utility in the production of di-carboxylic acid compounds from glucose.

34 Claims, 5 Drawing Sheets

(56) References Cited

U.S. PATENT DOCUMENTS

| 8,669,397 B2 | 3/2014 | Boussie et al. |
| 2010/0317822 A1 | 12/2010 | Boussie et al. |
| 2010/0317823 A1 | 12/2010 | Boussie et al. |
| 2011/0160483 A1* | 6/2011 | Rezkallah ............... C07C 51/47 562/554 |
| 2013/0158255 A1 | 6/2013 | Archer et al. |
| 2013/0225785 A1 | 8/2013 | Dias et al. |

OTHER PUBLICATIONS

Ericsson et al., "Anion-Exchange Chromatography of Dicarboxylic Hydroxy Acids", Journal of Chromatography, vol. 134, 1977, pp. 337-342.

Niu et al., "Benzene-Free Synthesis of Adipic Acid", Biotechnol. Prog., vol. 18, 2002, pp. 201-211.

Jansen et al., "Separation of Dicarboxylic Hydroxy Acids by Anion-Exchange Chromatography and Gas Chromatography", Journal of Chromatography, vol. 57, 1971, pp. 353-364.

International Search Report and Written Opinion received for PCT Application No. PCT/US2012/067436, mailed on Feb. 12, 2013, 12 pages.

Rokushika et al., "Anion Chromatography of Carboxylic Acids and Keto Acids Using a Hollow-Fibre Suppressor", Journal of Chromatography, vol. 253, 1982, pp. 87-94.

Tanaka et al., "Separation of Carboxylic Acids on a Weakly Acidic Cation-Exchange Resin by Ion-Exclusion Chromatography", Journal of Chromatography, vol. 850, 1999, pp. 187-196.

Novasep Process: Advanced Purification Technologies for Bio-Based Chemicals, Frontiers Bio-Refining 2012, 24 pages.

* cited by examiner

PROCESS FOR THE SEPARATION OF MONO- AND DI-CARBOXYLIC ACID COMPOUNDS

CROSS-REFERENCE TO RELATED APPLICATION

This application claims the benefit under 35 U.S.C. 119(e) of U.S. Provisional Application No. 61/570,624, filed on Dec. 14, 2011, the disclosure of which is hereby incorporated by reference in its entirety.

BACKGROUND

I. Field

The present disclosure relates generally to a process for the separation of mono- and di-carboxylic acid compounds; more specifically, to processes for the separation of at least one mono-carboxylic acid compound from a mixture comprising at least one mono-carboxylic acid compound and at least one di-carboxylic acid compound by selective elution from an ion exchange chromatography medium.

II. Description of Related Art

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see Ullmann's Encyclopedia of Industrial Chemistry, Wiley 2009 (7th edition), which is incorporated herein by reference.

For many years there has been an interest in using biorenewable materials such as carbohydrates (e.g. glucose derived from starch, cellulose or sucrose) as a feedstock to replace or supplement crude oil. See, for example, Klass, Biomass for Renewable Energy, Fuels, and Chemicals, Academic Press, 1998, which is incorporated herein by reference. Moreover, there have been efforts to produce adipic acid from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987. The conversion of carbohydrates into value-added chemicals generates carboxylic acid compounds, including mono-carboxylic acid compounds and di-carboxylic acid compounds. Separation and purification of the mono-carboxylic acid compounds and di-carboxylic acid compounds is desirable. One technique for separating mono-carboxylic acids from di-carboxylic acids is disclosed in U.S. Pat. No. 6,284,904. The methods disclosed in the '904 patent require use of strong inorganic acids such as $H_2SO_4$, HCl, nitric acid, and phosphoric acid. Use of such strong acids in aqueous solution presents a variety of challenges that must be met for commercial viability. Among them are the costs associated with having to employ and handle strong acids, both the need to employ special materials for the separation equipment and to handle the removed separation product containing such acids, and the downstream environmental costs associated with separation of the strong acids from the desired product and disposal of unreuseable spent strong acids. The production of chemicals from polyhydroxyl-containing substrates (e.g., glucaric acid), and especially for the production of chemicals from polyhydroxyl-containing biorenewable materials (e.g., glucose derived from starch, cellulose or sucrose) to important chemical intermediates such as adipic acid have been reported in U.S. Patent App. Pubs. US2010/0317822 and US2010/0317823, both of which are hereby incorporated by reference in their entireties. In US2010/0317823, processes for the conversion of glucose to an adipic acid product via glucaric acid or derivatives thereof are reported. Such processes include the steps of catalytic oxidation of glucose to glucaric acid or derivatives thereof followed by catalytic hydrodeoxygenation of glucaric acid or derivatives thereof to an adipic acid product. The catalytic oxidation step produces glucaric acid and derivatives which are subsequently hydrodeoxygenated to form an adipic acid product. In addition to glucaric acid and derivatives, mono-carboxylic acid intermediates and other di-carboxylic acid side products are formed in the oxidation reaction and some unreacted glucose may be present. The mono-carboxylic acid compounds and unreacted glucose, if separated from the di-carboxylic acid compounds, may be recycled to the oxidation reactor to increase overall yield of the adipic acid product. However, the recycle streams should not contain added components that could adversely affect the oxidation reaction. Moreover, the separated di-carboxylic acid compounds-containing solution that is supplied to the hydrodeoxygenation reaction should not, to the extent possible, impose additional costs to the process by requiring special materials of construction to enable the separation and/or handling of the separated products. Moreover, the supply of the di-acid compounds to the hydrodeoxygenation reaction should not introduce chemicals thereto which can cause the formation of unwanted reaction products which would adversely impact the efficiency and productivity of the reaction and/or adversely impact the downstream processing of the product stream from the hydrodeoxygenation reaction. Thus, there remains a need for processes for the separation of mono- and di-carboxylic acid compounds which avoids the potential adverse impact of employing strong acids.

SUMMARY

Briefly, therefore, the present invention is directed to process for separation of at least one di-carboxylic acid compound or at least one mono-carboxylic acid compound from a mixture. In accordance with one embodiment, the process is for the separation of at least one di-carboxylic acid compound from a mixture comprising at least one mono-carboxylic acid compound and at least one di-carboxylic acid compound, the process comprising the steps of: (a) contacting the mixture with an ion exchange chromatography medium to cause at least one mono-carboxylic acid compound and at least one di-carboxylic acid compound to be retained by the ion exchange chromatography medium; (b) eluting at least one mono-carboxylic acid compound from the ion exchange chromatography medium using a first eluent to form a first eluate; and (c) eluting at least one di-carboxylic acid compound from the ion exchange chromatography medium using a second eluent to form a second eluate; wherein the first eluate is enriched in at least one mono-carboxylic acid compound retained by the medium relative to the concentration of such acid in the first eluent, the second eluate is enriched in a least one di-carboxylic acid compound retained by the medium relative to the concentration of such acid in the second eluent, and at least one eluent comprises an organic acid. In accordance with another embodiment, the ion exchange chromatography medium is an anion exchange chromatography medium. In accordance with another embodiment, the first eluent comprises an organic acid having a pKa equal to or greater than about 3.7. In accordance with another embodiment, the second eluent comprises an organic acid having a pKa equal to or greater than about 3.7. In accordance with another embodiment, the first eluent and the second eluent comprise an organic acid. In accordance with another embodiment, the first eluent and the second eluent comprise the same organic acid, and wherein the concentration of the organic acid in the second eluent is greater than the concentration of the organic acid in the first eluent. In accordance with another embodiment, the first eluent and the second eluent comprise an organic acid, and wherein the organic acid is acetic acid. In accordance with another embodiment, the first eluent comprises up to about 30 vol % acetic acid in water, and wherein the second eluent comprises from about 30 vol % to about 100 vol % acetic acid in water and wherein the concentration of acetic acid in the second eluent is greater than the concentration of acetic acid in the first eluent. In accordance with another embodiment, the first eluent comprises about 1-20 vol % acetic acid in water, and wherein the second eluent comprises about 40-90 vol % acetic acid in water. In accordance with another embodiment, the first eluent comprises about 1-20 vol % acetic acid in water, and wherein the second eluent comprises about 50-90 vol % acetic acid in water. In accordance with another embodiment, the at least one mono-carboxylic acid compound is selected from the group consisting essentially of C6 mono-carboxylic acid compounds. In accordance with another embodiment, the at least one di-carboxylic acid compound is selected from the group consisting essentially of C6 di-carboxylic acid compounds. In accordance with another embodiment, at least one mono-carboxylic acid compound retained by the medium is a compound of formula I:

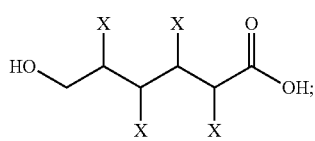

wherein each X is independently hydroxyl, oxo, acyloxy or hydrogen. In accordance with another embodiment, at least one mono-carboxylic acid compound retained by the medium is selected from the group consisting of gluconic acid, ketogluconic acids, and glucuronic acids. In accordance with another embodiment, at least one di-carboxylic acid compound retained by the medium is selected from the group consisting of C2-C6 di-carboxylic acid compounds. In accordance with another embodiment, at least two di-carboxylic acid compounds are retained by the medium and such compounds are selected from the group consisting of C2, C4, and C6 di-carboxylic acid compounds and wherein at least one of such compounds is glucaric acid. In accordance with another embodiment, at least one di-carboxylic acid compound retained by the medium is a compound of formula II:

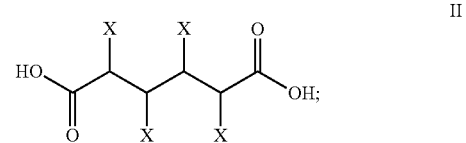

wherein each X is independently hydroxyl, oxo, acyloxy or hydrogen. In accordance with another embodiment, at least two di-carboxylic acid compounds are retained by the medium and the compounds are glucaric acid and at least one of tartaric acid and oxalic acid. In accordance with another embodiment, at least one mono-carboxylic acid compound retained by the medium is gluconic acid and at least one di-carboxylic acid compound is glucaric acid. In accordance with another embodiment, the first eluate comprises at least about 50 wt % of the at least one mono-carboxylic acid compound retained by the ion exchange chromatography medium. In accordance with another embodiment, the first eluate comprises at least about 60 wt % of the at least one mono-carboxylic acid compound retained by the ion exchange chromatography medium. In accordance with another embodiment, the first eluate comprises at least about 70 wt % of the at least one mono-carboxylic acid compound retained by the ion exchange chromatography medium. In accordance with another embodiment, the first eluate comprises at least about 80 wt % of the at least one mono-carboxylic acid compound retained by the ion exchange chromatography medium. In accordance with another embodiment, the first eluate comprises at least about 90 wt % of the at least one mono-carboxylic acid compounds retained by the ion exchange chromatography medium. In accordance with another embodiment, the second eluate comprises at least about 50 wt % of the at least one di-carboxylic acid compound contacted with the ion exchange chromatography medium. In accordance with another embodiment, the second eluate comprises at least about 60 wt % of the at least one di-carboxylic acid compound contacted with the ion exchange chromatography medium. In accordance with another embodiment, the second eluate comprises at least about 70 wt % of the at least one di-carboxylic acid compound retained by the ion exchange chromatography medium. In accordance with another embodiment, the second eluate comprises at least about 80 wt % of the at least one di-carboxylic acid compound retained by the ion exchange chromatography medium. In accordance with another embodiment, the second eluate comprise at least about 90 wt % of the at least one di-carboxylic acid compound retained by the ion exchange chromatography medium. In accordance with another embodiment, the ion exchange chromatography medium is selected from the group consisting of Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Finex AS532, Finex AS510, and Dowex Retardion 11A8. In accordance with another embodiment, the ion exchange chromatography medium is selected from the group consisting of Mitsubishi Diaion UBA100S, Mitsubishi Diaion UMA150, Mitsubishi Diaion UMA130J, Finex AS532, and Mitsubishi Diaion SA21. In accordance with another embodiment, the ion exchange chromatography medium is selected from the group consisting of Mitsubishi Diaion UBA100S, Finex AS532, and Mitsubishi Diaion UMA150. In accordance with another embodiment, the ion exchange chromatography medium is Mitsubishi Diaion UBA100S. In accordance with another embodiment, the ion exchange chromatography medium is Mitsubishi Diaion UMA150. In accordance with another embodiment, the first and second eluent comprise formic acid. In accordance with another embodiment, the first eluent and the second eluent comprise about 0.5-10 vol % formic acid. In accordance with another embodiment, the first eluent and the second eluent comprise about 3-7 vol % formic acid. In accordance with another embodiment, the first eluent and the second eluent comprise about 4-6 vol % formic acid. In accordance with another embodiment, the first eluent and second eluent comprise about 5 vol % formic acid. In accordance with another embodiment, at least one mono-carboxylic acid compound comprises a mono-carboxylic acid in equilibria with one or more lactones thereof. In accordance with another embodiment, at least one di-carboxylic acid compound comprises a di-carboxylic acid in equilibria with at least one mono- or di-lactones thereof. In accordance with another embodiment, at least one di-carboxylic acid compound comprises glucaric acid and at least one mono- or di-lactones, which lactones are selected from the group consisting of glucaro-1,4-lactone, glucaro-1,4:3,6-dilactone, and glucaro-3,6-lactone. In accordance with another embodiment, the ion-exchange chromatography is carried out using simulated moving bed (SMB) chromatography. In accordance with another embodiment, the mixture comprises about 1-60 wt % dissolved solids. In accordance with another embodiment, the mixture comprises about 1-50 wt % dissolved solids. In accordance with another embodiment, the mixture comprises about 1-40 wt % dissolved solids. In accordance with another embodiment, at least about 50,000 pounds (avoir) of at least one di-carboxylic acid compound is eluted per hour. In accordance with another embodiment, the eluting is carried out using isocratic elution conditions or gradient elution conditions. In accordance with another embodiment, the mixture is derived from the oxidation of glucose. In accordance with another embodiment, the process for the separation also comprises a process for the production of an adipic acid product, the adipic acid process comprising the steps of oxidizing glucose to produce a mixture comprising at least one mono-carboxylic acid compound and at least one di-carboxylic acid compound, separating at least one mono-carboxylic acid compound in the mixture from at least one di-carboxylic acid compound in the mixture by any of the separation processes disclosed herein, and converting at least a portion of at least one di-carboxylic acid separated from the mixture to an adipic acid product. In accordance with one embodiment, at least one di-carboxylic acid compound converted to an adipic acid product is glucaric acid. In accordance with another embodiment, the mixture further comprises glucose. In accordance with another embodiment, the separation process is carried out at a temperature between 0° C. and 100° C. In accordance with another embodiment, the separation process is carried out at a temperature between 10° C. and 90° C. In accordance with another embodiment, the separation process is carried out at a temperature between 20° C. and 80° C. In accordance with another embodiment, a volume of ion exchange chromatography medium resides in a bed, and wherein the elution of the at least one mono-carboxylic acid compound and the at least one di-carboxylic acid compound is essentially completed using a total volume of medium equal to less than about 20 times the volume contained in such bed. In accordance with another embodiment, the total volume is equal to or less than about 10 times the volume contained in such bed. In accordance with another embodiment, the total volume is equal to or less than about 5 times the volume contained in such bed. In accordance with another embodiment, the number of beds employed to hold such total volume and effect such elution is equal to or less than 20. In accordance with another embodiment, the number of beds employed to hold such total volume and effect such elution is equal to or less than 10. In accordance with another embodiment, the number of beds employed to hold such total volume and effect such elution is equal to or less than 5.

The present invention is further directed to a process for the separation of at least one mono-carboxylic acid compound or at least one di-carboxylic acid compound from a mixture, the process comprising the steps of: (a) contacting the mixture with an ion exchange chromatography medium to cause at least one mono-carboxylic acid compound or at least di-carboxylic acid compound to be retained by the ion exchange chromatography medium; and, (b) eluting at least one of the at least one mono-carboxylic acid compound or the at least one di-carboxylic acid compound from the ion exchange chromatography medium using an eluent to form an eluate; wherein the eluate is enriched in one of the at least one mono-carboxylic acid compound or the at least one di-carboxylic acid compound retained by the medium relative to the concentration of such eluted acid in the remainder of the mixture having contacted the medium and wherein the eluent comprises an organic acid. In accordance with one embodiment, the retained acid compound is at least one mono-carboxylic acid compound. In accordance with another embodiment, the retained acid compound is at least one di-carboxylic acid compound. In accordance with another embodiment, at least one di-carboxylic acid compound is substantially unretained by such medium. In accordance with another embodiment, at least one mono-carboxylic acid compound is substantially unretained by such medium. In accordance with another embodiment, the organic acid has a pKa of at least about 3.7. In accordance with another embodiment, the organic acid is acetic acid. In accordance with another embodiment, the eluent further comprises water. In accordance with another embodiment, the process for the separation also comprises a process for the production of an adipic acid product, the adipic acid process comprising the steps of oxidizing glucose to produce a mixture comprising at least one mono-carboxylic acid compound and at least one di-carboxylic acid compound, separating at least one mono-carboxylic acid compound in the mixture from at least one di-carboxylic acid compound in the mixture by any of the separation processes disclosed herein, and converting at least a portion of at least one di-carboxylic acid separated from the mixture to an adipic acid product. In accordance with one embodiment, at least one di-carboxylic acid compound converted to an adipic acid product is glucaric acid. In accordance with another embodiment, the mixture further comprises glucose. In accordance with another embodiment, the separation process is carried out at a temperature between 0° C. and 100° C. In accordance with another embodiment, the separation process is carried out at a temperature between 10° C. and 90° C. In accordance with another embodiment, the separation process is carried out at a temperature between 20° C. and 80° C. In accordance with another embodiment, a volume of ion exchange chromatography medium resides in a bed, and wherein the elution of the at least one mono-carboxylic acid compound and the at least one di-carboxylic acid compound is essentially completed using a total volume of medium equal to less than about 20 times the volume contained in such bed. In accordance with another embodiment, the total volume is equal to or less than about 10 times the volume contained in such bed. In accordance with another embodiment, the total volume is equal to or less than about 5 times the volume contained in such bed. In accordance with another embodiment, the number of beds employed to hold such total volume and effect such elution is equal to or less than 20. In accordance with another embodiment, the number of beds employed to hold such total volume and effect such elution is equal to or less than 10. In accordance with another embodiment, the number of beds employed to hold such total volume and effect such elution is equal to or less than 5. In accordance with another embodiment, the ion exchange chromatography medium is an anion exchange chromatography medium.

DETAILED DESCRIPTION

Figure 1:
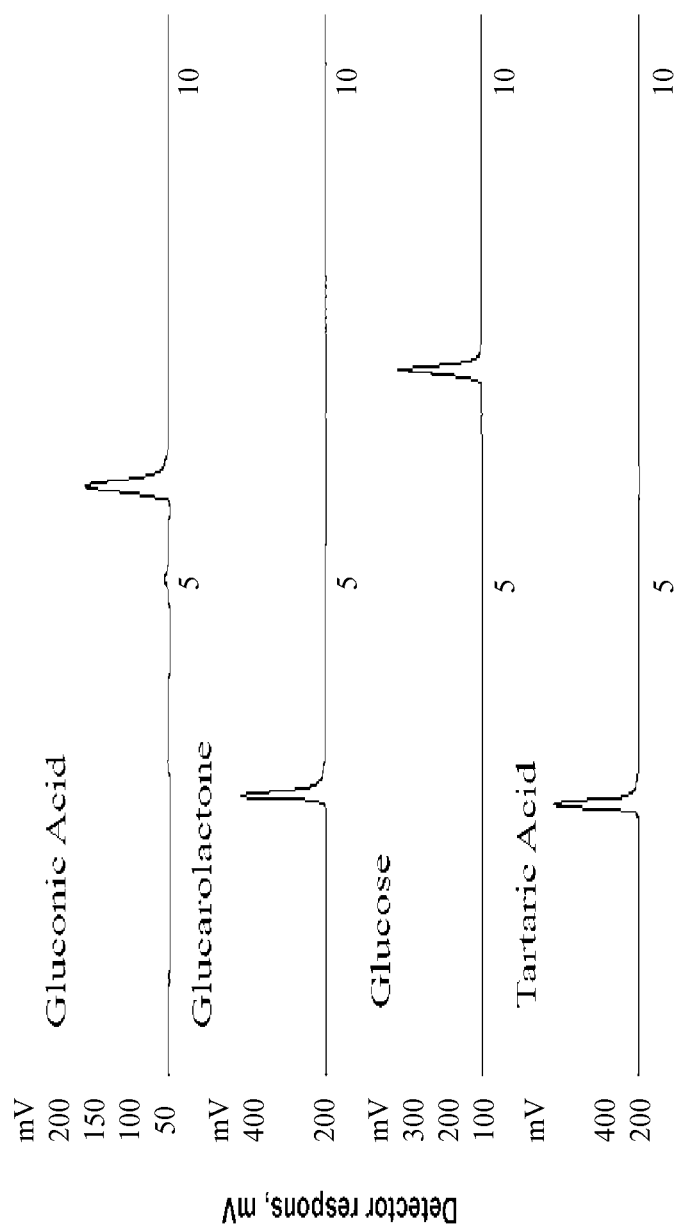
FIG. 1 depicts analytical HPLC traces for glucose, gluconic acid, glucaric acid, and tartaric acid.

The following description sets forth exemplary processes, parameters and the like. It should be recognized, however, that such description is not intended as a limitation on the scope of the present invention.

As used herein, the term "about" means approximately, in the region of, roughly, or around. When the term "about" is used in conjunction with a numerical range, it modifies that range by extending the boundaries above and below the numerical values set forth.

As used herein, the term "glucaric acid" collectively refers to glucaric acid and derivatives thereof. The glucaric acid may be substantially pure or may exist in a mixture that includes any amount of one or more derivatives of glucaric acid. Similarly, the one or more derivatives may be substantially pure or may include any amount of one or more derivatives of glucaric acid and/or glucaric acid itself. Derivatives of glucaric acid include "glucarolactones," which include mono- or di-lactones of glucaric acid such as D-glucaro-1,4-lactone, D-glucaro-6,3-lactone, and D-glucaro-1,4:6,3-dilactone. Other derivatives include salts, esters, ketones, and halogenated forms of glucaric acid.

As used herein, the term "mono-carboxylic acid compounds" collectively refers to substantially pure mono-carboxylic acid compounds or may include any amount of one or more derivatives of the mono-carboxylic acid compounds such as lactones, salts, esters, ketones, halogenated forms of the mono-carboxylic acid compounds, or any mixture thereof in any combination. Non-limiting examples of the mono-carboxylic acid compounds described herein include C6 mono-carboxylic acid compounds, gluconic acid, ketogluconic acids, glucuronic acid, or any mixture thereof in any combination.

As used herein, the term "di-carboxylic acid compounds" refers to substantially pure di-carboxylic acid compounds or may include any amount of one or more derivatives of the di-carboxylic acid compounds such as lactones, salts, esters, ketones, halogenated forms of the di-carboxylic acid compounds, alone, or any mixture thereof in any combination. Non-limiting examples of the di-carboxylic acid compounds described herein include C2-C6 di-carboxylic acid compounds, glucaric acid, 2,3,4-trihydroxypentanedioic acid, tartaric acid, 2-hydroxymalonic acid, or oxalic acid, alone, or any mixture thereof in any combination.

The present invention provides processes for the separation of at least one mono-carboxylic acid compound or at least one di-carboxylic acid compound from a mixture employing chromatography. In various embodiments, the process of separation is ion exchange chromatography. Generally, the process comprises: (a) contacting the mixture with an ion exchange chromatography medium to cause at least one mono-carboxylic acid compound or at least one di-carboxylic acid compound to be retained by the ion exchange chromatography medium; and (b) eluting at least one mono-carboxylic acid compound or at least one di-carboxylic acid compound from the ion exchange chromatography medium using an eluent to form an eluate; wherein the eluate is enriched in one of the at least one mono-carboxylic acid compound or the at least one di-carboxylic acid compound retained by the medium relative to the concentration of such eluted acid in the remainder of the mixture having contacted the medium and wherein the eluent comprises an organic acid. In many embodiments of the general process, the pKa of the eluent is equal to or greater than about 3.7. In another embodiment, the organic acid is acetic acid. In another embodiment, the eluent further comprises water. In another embodiment, the retained acid compound is at least one mono-carboxylic acid compound. In another embodiment, the retained acid compound is at least one di-carboxylic acid compound. In another embodiment, at least one mono-carboxylic acid compound is substantially unretained by such medium. In another embodiment, at least one di-carboxylic acid compound is substantially unretained by such medium.

In various embodiments, the mixture comprises at least one mono-carboxylic acid compound and at least one di-carboxylic acid compound, and the process comprises the steps of: (a) contacting the mixture with an ion exchange chromatography medium to cause at least one mono-carboxylic acid compound and at least one di-carboxylic acid compound to be retained by the ion exchange chromatography medium; (b) eluting at least one mono-carboxylic acid compound from the ion exchange chromatography medium using a first eluent to form a first eluate; and (c) eluting at least one di-carboxylic acid compound from the ion exchange chromatography medium using a second eluent to form a second eluate; wherein the first eluate is enriched in at least one mono-carboxylic acid compound retained by the medium relative to the concentration of such acid in the first eluent, the second eluate is enriched in a least one di-carboxylic acid compound retained by the medium relative to the concentration of such acid in the second eluent, and at least one eluent comprises an organic acid. Typically, the ion exchange chromatography medium has a different retention strength for the di-carboxylic acid compounds in comparison to its retention strength for the mono-carboxylic acid compounds. In various preferred embodiments the first eluent comprises an organic acid having a pKa equal to or greater than about 3.7. In various other preferred embodiments, the second eluent comprises an organic acid having a pKa equal to or greater than about 3.7. In still more preferred embodiments, the first eluent and the second eluent comprise the same organic acid. In yet other more preferred embodiments the first eluent and the second eluent comprise the same organic acid and the concentration of the organic acid in the second eluent is greater than the concentration of the organic acid in the first eluent. In preferred embodiments, the first and second eluents comprise acetic acid.

Suitable preferred ion exchange chromatography media are weak anion or strong anion exchange resins. In various embodiments, the ion exchange chromatography medium is selected from the group consisting of Mitsubishi Diaion WA30, Mitsubishi Diaion WA20, Mitsubishi Diaion UBA100S, Mitsubishi Diaion UMA150, Mitsubishi Diaion UMA130J, Mitsubishi Diaion SA21, Dowex Retardion 11A8, Finex AS510, and Finex AS532. In other embodiments, the ion exchange chromatography medium is selected from the group consisting of Mitsubishi Diaion UBA100S, Mitsubishi Diaion UMA150, Mitsubishi Diaion UMA130J, Finex AS532, and Mitsubishi Diaion SA21. In some preferred embodiments, the ion exchange chromatography medium is selected from the group consisting of Mitsubishi Diaion UBA100S, Finex AS532, and Mitsubishi Diaion UMA150.

Typically, the ion exchange chromatography medium is packed into a chromatographic separation apparatus which may include one or more chromatography columns. In some embodiments, the ion-exchange chromatography is carried out using simulated moving bed (SMB) chromatography. In general, the ion exchange chromatography medium may encompass a variety of resin particle sizes and functional group loadings when used in the separation processes disclosed herein.

Generally, the ion exchange chromatography medium is conditioned prior to the separation of mono-carboxylic acid compounds from and di-carboxylic acid compounds. For weak anion resins, the conditioning may include contacting the anion exchange chromatography medium with aqueous organic acid solutions having a pKa equal to or greater than about 3.7 to protonate the resin to the desired form, for example acetate or formate. For some strong anion resins containing chloride, the chloride may be converted to the hydroxide form by contacting the resin with multiple bed volumes (e.g., 20 or more bed volumes) of a NaOH solution followed by washing the resin with multiple bed volumes (e.g., 10 or more bed volumes) of de-ionized water. The hydroxide form may then be contacting with the organic acid solution, such as acetic or formic acid, to produce the desired anion form. For other strong anion resins containing chloride, the resins may be conditioned in situ by performing a blank aqueous acid gradient elution with multiple bed volumes (e.g., 20 or more bed volumes).

After the one or more chromatography columns have been packed with the desired ion exchange chromatography medium, and the ion exchange chromatography medium has been conditioned, the mixture containing at least one mono-carboxylic acid compound and at least one di-carboxylic acid compound is loaded onto the column. The ion exchange chromatography may be carried out in a batch, semi-continuous, or continuous process. Generally, at least one di-carboxylic acid compound will be retained by the ion exchange chromatography medium. In those embodiments in which both mono- and di-carboxylic acid compounds are retained by the ion exchange medium, at least one di-carboxylic acid compound will be retained more strongly to the ion exchange chromatography medium than at least one mono-carboxylic acid compound. After contacting the mixture to the ion exchange chromatography medium, at least one mono-carboxylic acid compound will be eluted using a first eluent to form a first eluate enriched in at least one mono-carboxylic acid compound relative to the concentration of such acid in the first eluent. After elution with the first eluent, at least one di-carboxylic acid compounds may be eluted using a second eluent to form a second eluate enriched in at least one di-carboxylic acid compound retained by the medium relative to the concentration of such acid in the second eluent. In preferred embodiments, at least one eluent includes an organic acid. In some embodiments, the first eluate comprises at least about 50 wt %, 60 wt %, 70 wt %, 80 wt %, or 90 wt % of at least one mono-carboxylic acid compound retained by the ion exchange chromatography medium. In some embodiments, the second eluate comprises at least about 50 wt %, 60 wt %, 70 wt %, 80 wt %, or 90 wt % of at least one di-carboxylic acid compound retained by the ion exchange chromatography medium.

Typically, the amount of compounds present in the mixture will affect the separation. Generally, the mixture comprises about 1-60 wt % of such compounds. More typically, the mixture comprises about 1-50 wt %, and in many instances about 1-40 wt %, dissolved solids.

Generally, the first and second eluents may be the same or different and may contain an organic acid. The first eluant may be water or may contain an organic acid. The second eluant contains an organic acid. When the first eluant is water the first and second eluents are different, and when the first eluant contains an organic acid the first and second eluents may be the same or different. In some embodiments, the eluents consist essentially of organic acids. A variety of elution conditions may be employed. In various preferred embodiments, the first eluent comprises an organic acid having a pKa equal to or greater than about 3.7. In various other preferred embodiments, the second eluent comprises an organic acid having a pKa equal to or greater than about 3.7. Non-limiting examples of such acids are formic acid and acetic acid. The eluents may be deployed under isocratic elution conditions or gradient elution conditions. In some embodiments, the first eluent and the second eluent comprise about 0.5-10 vol %, 3-7 vol %, 4-6 vol % or 5 vol % formic acid. In some preferred embodiments, the first eluent comprises about 1-30 vol % or 1-20 vol % acetic acid in water. In some preferred embodiments, the second eluent comprises about 30-100 vol %, 40-90 vol %, or 50-90 vol % acetic acid. In other more preferred embodiments, the first eluent and the second eluent comprise acetic acid. In yet other more preferred embodiments, the first eluent comprises up to about 20-30 vol % acetic acid in water and the second eluent comprises about 30-100 vol %, 40-90 vol %, or 50-90 vol % acetic acid.

The separation processes may be conducted at laboratory scale, pilot plant scale, demonstration plant scale, or commercial scale. In some embodiments, about 50,000-70,000 pounds (avoir) of at least one di-carboxylic acid compound is eluted per hour. In some embodiments, about 20-50 pounds of at least one di-carboxylic acid compound is eluted per hour. In some embodiments, about 1-10 pounds of at least one di-carboxylic acid compound is eluted per hour. Typically, substantially lesser amounts of mono-carboxylic acids pass through the ion exchange medium or are eluted therefrom in processes in which the di-carboxylic acid is the desired reaction product, such as in the production of adipic acid from glucose containing feeds as described, for example, in U.S. Patent App. Pubs. US2010/0317822 and US2010/0317823.

It should be recognized that the operating conditions for the separation process may be adjusted to balance the rates at which the di-carboxylic acids are eluted with both the separation efficiency and the concentration of the eluate. For example, it is known that higher dilution, slower flow rates, and lower temperatures can provide better chromatographic separation; however, this may come at the expense of lower overall throughput and require a lengthy downstream concentration operation. Conversely, throughput and eluate concentration can be increased at lower dilution, faster flow rates, and higher temperatures, but the separation of mono-carboxylic acid compounds from di-carboxylic acid compounds may not be as efficient. Furthermore, these properties can change as a function of the scale and chromatography hardware, such that the best conditions may be different at the laboratory, pilot plant, demonstration plant, and commercial plant scales. It is our intent that the operating conditions be chosen to optimize the separation, throughput, and eluate concentration at each of these scales. Moreover, in some embodiments, the eluting may be carried out using isocratic or gradient elution conditions.

Preferred operating temperatures for the separation are between 0° C. and 100° C. More preferred temperatures are between about 10° C. and about 90° C. Even more preferred temperatures are between about 20° C. and about 80° C.

Typically, the volume of ion exchange chromatography medium resides in a bed. In some embodiments, elution of at least one mono-carboxylic acid compound and/or at least one di-carboxylic acid compound is essentially completed using a total volume of medium equal to less than about 20 times the volume contained in such bed. In some preferred embodiments, the total volume is equal to or less than about 10 times the volume contained in such bed. In yet other preferred embodiments, the total volume is equal to or less than about 5 times the volume contained in such bed. In the preceding embodiments, the number of beds employed to hold such total volume and effect such elution is equal to or less than 20, 10, or 5.

After separation of the mono-carboxylic acid compounds from the di-carboxylic acid compounds, however effected in accordance with the disclosure herein, each may be further purified by a variety of techniques known in the art such as crystallization, distillation, extraction, chromatography, any other purification method, or any combination thereof.

In some embodiments, the mono-carboxylic acid compound is selected from the group consisting essentially of C6 mono-carboxylic acid compounds. In some embodiments, the di-carboxylic acid compound is selected from the group consisting essentially of C6 di-carboxylic acid compounds. In some preferred embodiments, at least one mono-carboxylic acid compound is selected from the group consisting of gluconic acid, ketogluconic acids, and glucuronic acids. In other preferred embodiments, at least one di-carboxylic acid compound is selected from the group consisting of C2-C6 di-carboxylic acid compounds. In other preferred embodiments, at least one di-carboxylic acid compound is selected from the group consisting of glucaric acid, 2,3,4-trihydroxypentanedioic acid, tartaric acid, 2-hydroxymalonic acid, and oxalic acid. In yet other preferred embodiments, at least two di-carboxylic acid compounds are retained by the medium and such compounds are selected from the group consisting of C2, C4, and C6 di-carboxylic acid compounds and at least one of such compounds is glucaric acid. In yet other preferred embodiments, at least two di-carboxylic acid compounds are retained by the medium and the compounds are glucaric acid and at least one of tartaric acid and oxalic acid. In yet other preferred embodiments, at least one mono-carboxylic acid compound is retained by the medium and it is gluconic acid and at least one di-carboxylic acid compound retained by the medium is glucaric acid.

In certain preferred embodiments, at least one mono-carboxylic acid compound retained by the medium is a compound of formula I:

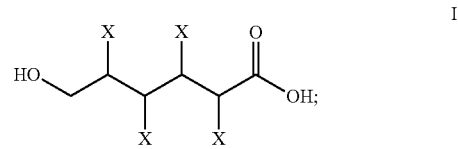

wherein each X is independently hydroxyl, oxo, acyloxy or hydrogen. Salt and lactone forms of the compound of formula I are contemplated. Salt forming ions include, without limitation, for example ammonium ions and metal ions (e.g., alkali and alkaline earth metals). In various embodiments, the compound of formula I comprises gluconic acid. In some embodiments, at least one mono-carboxylic acid compound comprises a mono-carboxylic acid in equilibria with one or more lactones thereof.

In certain preferred embodiments, the at least one di-carboxylic acid compound retained by the medium is a compound of formula II:

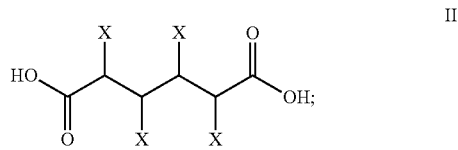

wherein each X is independently hydroxyl, oxo, acyloxy or hydrogen. Salt and mono- or di-lactone forms of the compound of formula II are contemplated. Salt forming ions include, without limitation, for example ammonium ions and metal ions (e.g., alkali and alkaline earth metals). In various preferred embodiments, the compound of formula II comprises glucaric acid. In some embodiment, at least one di-carboxylic acid compound comprises a di-carboxylic acid in equilibria with at least one mono- or di-lactones thereof.

In particular embodiments of the present invention, the mixture containing at least one mono-carboxylic acid compound and at least one di-carboxylic acid compound is generated from a biorenewable material such as glucose. In such embodiments, the mixture containing the at least one mono-carboxylic acid compound and at least one di-carboxylic acid compound may contain unreacted glucose. Generally, when glucose is present during the separation, glucose is not retained as strongly on an ion exchange chromatography medium compared to the mono- or di-carboxylic acid compound(s), and the majority of glucose elutes in the first eluate. Without being bound by any theory, the ion exchange chromatography medium associates and retains molecules having a carboxylic acid moiety more strongly than molecules such as glucose that lack such a moiety.

In particular embodiments of the present invention, the separation is practiced to process a mixture of mono- and di-carboxylic acid compounds generated in a process to prepare an adipic acid product as described in US2010/0317823. In such a process for the production of an adipic acid product, the process includes the steps of oxidizing glucose to produce a mixture comprising at least one mono-carboxylic acid compound and at least one di-carboxylic acid compound, separating at least one mono-carboxylic acid compound in the mixture from at least one di-carboxylic acid compound in the mixture by any of the separation processes described above, and converting at least a portion of at least on di-carboxylic acid separated from the mixture to an adipic acid product. In a preferred embodiment, glucaric acid, a di-carboxylic acid compound, will be hydrodeoxygenated to produce an adipic acid product. After separation of glucaric acid from the mono-carboxylic acids, the mono-carboxylic acids and unreacted glucose, if any, may be recycled to the oxidation reactor where the mono-carboxylic acid compounds and any unreacted glucose may be further oxidized to glucaric acid, increasing overall yield of the adipic acid product. In various embodiments, the second eluate may be directly introduced into a hydrodeoxygenation reactor to produce an adipic acid product.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

I. General Procedures

The testing of commercially-available, anion-exchange resins was conducted using a Gilson preparative liquid chromatograph fitted with a 2 cm ID×3 cm length column packed with the candidate resin. The detection technique was an ELSD connected on-line after a UV detector. Flow rates, mobile phase compositions and gradients are described in the sections below. Experiments were conducted at room temperature.

II. Anion-Exchange Resins

Exemplary anion-exchange resins tested in the Examples are listed in Table 1. All resins were conditioned prior to testing. All weak anion resins were received in the free-base form and contact with aqueous acid solutions served to protonate the resin to the desired form (acetate or formate). Type I strong anion resin Mitsubishi Diaion UBA100S was transformed from the chloride form (as received) to the hydroxide form by contacting 20 bed volumes of 1N NaOH solution followed by 10 bed volumes of de-ionized water. The resin was loaded in the hydroxide form with aqueous acid contact (acetic acid or formic acid) giving the desired anion form through acid-base neutralization. Type II strong anion resin Mitsubishi Diaion SA21A and Type I strong anion resin Dowex Retardion 11A8 were received in the chloride form and conditioned in situ by performing a blank aqueous acid gradient elution (typically >20 bed volumes total elution).

TABLE 1

Exemplary Anion-Exchange Resins

| Resin ID | Manufacturer | Type | Matrix | Mean particle size/ μm | Uniformity coefficient | Functional group loading/ eq $L^{-1}$ | Moisture/ wt % |
|---|---|---|---|---|---|---|---|
| Amberlite IRA-67 | Rohm & Haas | Weak anion, tertiary amine | Acrylic | 632 | 1.49 | 1.72 | 60 |
| Diaion UBA100S | Mitsubishi | Strong anion, Type 1 | PS/DVB | 174 | 1.04 | 1.43 | 48 |
| Diaion WA10 | Mitsubishi | Weak anion, tertiary amine | Acrylic | >350 | <1.6 | >1.2 | 63-69 |
| Diaion WA20 | Mitsubishi | Weak anion, secondary amine | PS/DVB | 440 | 1.4 | 2.7 | 43 |
| Diaion WA30 | Mitsubishi | Weak anion, tertiary amine | PS/DVB | 490 | 1.6 | 1.6 | 50 |
| Dioaion SA21A | Mitsubishi | Strong anion, Type II | PS/DVB | >400 | <1.6 | >0.8 | 55-65 |
| Dowex Retardion 11A8 | Dowex | Strong anion, Type I: weak acid (poly(acrylic acid)) | PS/DVB | ~250 | | | 45 |
| Diaion UMA150 | Mitsubishi | Strong anion, Type 1 | PS/DVB | 220 | 1.05 | 1.58 | 43 |
| AS532 | Finex | Strong anion, Type II | PS/DVB | 370 | | 1.06 | 55 |
| AS510 | Finex | Strong anion, Type I | PS/DVB | 300 | | 1.3 | 49 |

III. Analytical Procedures

Fractions collected from the testing of anion exchange resins were reanalyzed by HPLC or by ion chromatography separation.

HPLC Separation

Separations were carried out using an Agilent 1100 HPLC instrument with evaporative light scattering detector (ELSD). Sample injection volume was 10 µL. Samples were separated using a Neptune HILIC 150×4.6 mm column (5 µm particle size, 100 Å pore diameter, ES Industries Part#135221-NPN-SI) using the gradient elution listed below in Table 2 (solvent A=water-methanol 90:10 and solvent B=acetonitrile+0.1 vol % trifluoroacetic acid). FIG. 1 plots traces for four individual components analyzed in the following Examples.

TABLE 2

Analytical HPLC gradient elution conditions

| Time (min) | vol % B | Flow (mL/min) |
|---|---|---|
| 0.00 | 100.0 | 1.00 |
| 0.50 | 100.0 | 1.00 |
| 10.50 | 0.0 | 1.00 |
| 13.50 | 0.0 | 1.00 |
| 13.51 | 100.0 | 1.00 |
| 15.00 | 100.0 | 1.00 |

Ion Chromatography Separation

Ion chromatography separations were performed using a parallel Dionex ICS-3000 with the following components: 1) AS autosampler, 2) DP quaternary pump, 3) EG eluent generator (KOH, two KOH cartridges), 4) column compartment with two 10 µL sample loops and two Dionex IonPac AS11-HC 2×250 mm analytical columns plus two Dionex IonPac AG11-HC 2×50 mm guard columns, 5) detector compartment with two ASRS 300 suppressors and conductivity detectors, and 6) ESA Corona CAD detector after each conductivity detector.

Figure 2:
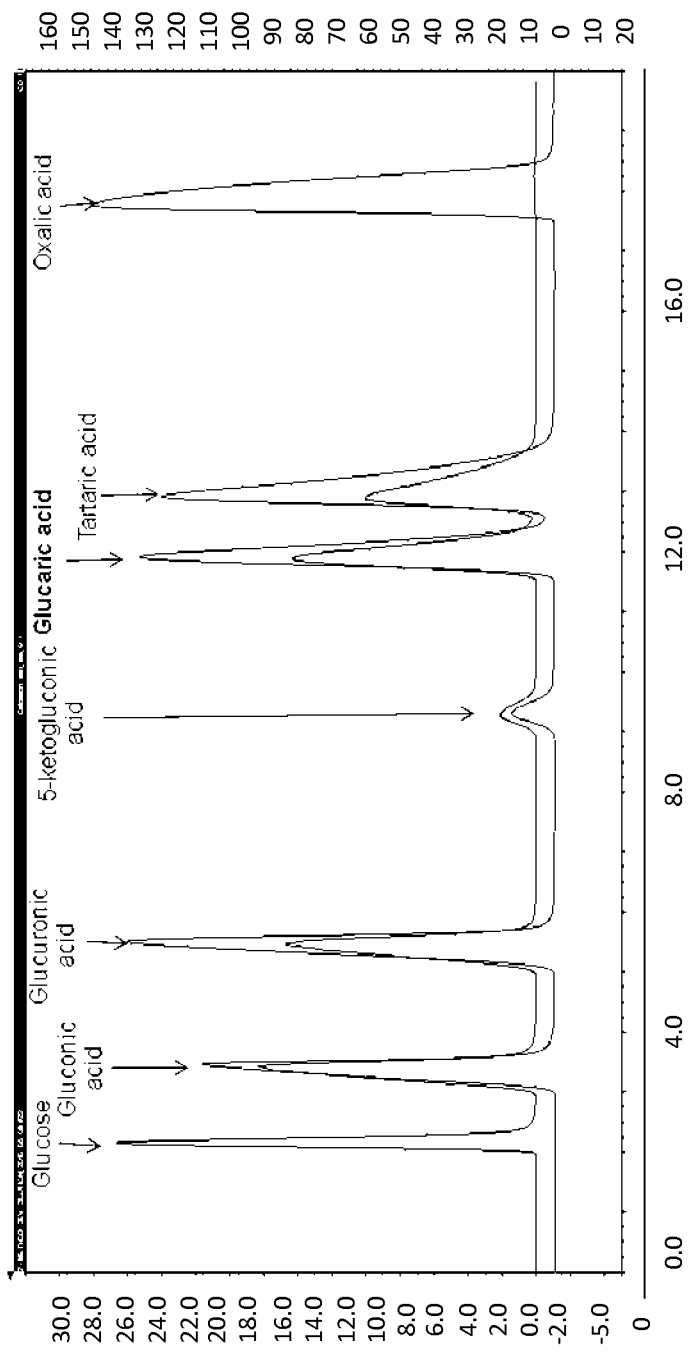
FIG. 2 depicts typical exemplary anion exchange chromatogram showing the Corona CAD detector trace (upper trace containing the glucose peak) and the conductivity detector trace (lower trace containing the oxalic acid peak).

Ion chromatography separations were performed with 0.22 µm filtered and degassed 18.2 MΩ-cm water at 25° C. Samples for were diluted to approximately 5 mM for analysis. This concentration enables detection by both conductivity and CAD with parabolic calibration (concentration=$ax^2+bx$, where x=analytical area). Reducing concentration to <0.5 mM enables linear calibration by conductivity at the expense of CAD detection. Table 3 lists the eluent generator gradient elution and FIG. 2 shows a typical chromatogram for the four components studied in the following Examples (glucose, gluconic acid, glucaric acid, and tartaric acid) plus three additional species (glucuronic acid, 5-ketogluconic acid, and oxalic acid).

TABLE 3

Ion Chromatography eluent generator gradient elution program

| Time/ mins | Flowrate/mL min$^{-1}$ | [KOH]/ mM | EGC curve |
|---|---|---|---|
| 0.00 | 0.55 | 1.00 | 5 |
| 0.10 | 0.55 | 4.00 | 5 |
| 7.00 | 0.55 | 4.00 | 5 |
| 7.10 | 0.55 | 9.00 | 5 |
| 14.00 | 0.55 | 5.00 | 5 |
| 17.10 | 0.55 | 25.00 | 5 |
| 18.00 | 0.55 | 25.00 | 5 |
| 18.10 | 0.55 | 1.00 | 5 |
| 20.00 | 0.55 | 1.00 | 5 |

Example 1

Separation of Components by Ion-Exchange Chromatography on Commercial Resins

Glucose, gluconic acid, glucaric acid, and tartaric acid were injected individually into selected resins using the Gilson preparative LC system. Mobile phase components were water and acetic acid.

The first seven resins listed in Table 1 were testing with the following method:

1) flow rates 2-5 mL/min, 2) gradient elution from 5-95 vol % acetic acid in water, 3) injections of 1 mL (200 mg/mL solutions), and 4) fractions were collected and re-analyzed by HPLC and/or ion chromatography.

The results illustrated that glucose was not retained under any conditions, and gluconic acid (a C6 mono-acid), eluted at lower acetic acid concentrations (5-30 vol % acetic acid), and D-glucaric acid and tartaric acid (another di-acid) eluted at higher acetic acid concentrations (50 vol % acetic acid). These results demonstrate that, in accordance with the present invention, ion exchange chromatography can be employed wherein acetic acid is used under specific conditions to enable the separation and accumulation of D-glucaric acid in acetic acid from C6 mono-acids and unreacted glucose.

Example 2

Separation of Components by Ion-Exchange Chromatography on Select Commercial Resins The following resins were selected based on the results in Example 1: Mitsubishi Diaion UBA100S, DOWEX Retardion 11A8, and Mitsubishi Diaion SA21.

Glucose, gluconic acid, glucaric acid, and tartaric acid were injected individually into the Gilson preparative LC system. Mobile phase components were water and acetic acid.

A gradient elution condition was deployed using the following conditions:

1) flow rate 5 mL/min, 2) gradient elution with 5-50 vol % acetic acid in water, 3) injections of 0.25 mL (200 mg/mL solutions), and 4) fractions were collected and re-analyzed by HPLC and/or ion chromatography. Blank runs injected prior to and after each sample.

The order of retention of the components were tartaric acid>glucaric acid>gluconic acid>glucose. The results again illustrated that glucose was not retained under any conditions, and gluconic acid (a C6 mono-acid) eluted at lower acetic acid concentrations (5-30 vol % acetic acid), and glucaric acid and tartaric acid (another di-acid) eluted at higher acetic acid concentrations (50 vol % acetic acid). D-glucaric acid and tartaric acid eluted completely using 50 vol % acetic acid in water. Again, these results demonstrate that, in accordance with the present invention, ion exchange chromatography can be employed wherein acetic acid is used under specific conditions to enable the separation and accumulation of D-glucaric acid in acetic acid from C6 mono-acids and unreacted glucose.

Example 3

Separation of Components by Ion-Exchange Chromatography on Select Commercial Resins Aqueous solutions of gluconic acid, D-glucaric acid, and tartaric acid were injected individually into the Gilson preparative LC system. Mobile phase components were water and acetic acid.

The resin selected for separations tests was Mitsubishi UMA150. Isocratic elution conditions were deployed using the following acetic acid/water mobile phase compositions: 20 vol % acetic acid in water; 30 vol % acetic acid in water; 40 vol % acetic acid in water; 50 vol % acetic acid in water; 70 vol % acetic acid in water; 80 vol % acetic acid in water; and 90 vol % acetic acid in water.

The mobile phase compositions were deployed using the following conditions:
1) flow rate 20 mL/min,
2) injections of 1.00 mL (800 mg/mL solutions), and
3) fractions were collected and re-analyzed by HPLC and/or ion chromatography The results illustrated that gluconic acid, a mono acid, eluted at low acetic acid concentrations (20 vol % acetic acid) and that D-glucaric acid and tartaric acid (an "other C6 di-acid") may be eluted at higher acetic acid concentrations (40-90 vol % acetic acid). These results demonstrate that components of interest may be separated and the solvent composition changed from the initial D-glucaric acid solvent composition of 100% water to about 90 vol % acetic acid/10 vol % water using ion exchange chromatography, which solution would be a more preferred hydrodeoxygenation substrate.

Example 4

Separation of Gluconic and Glucaric Acid by Ion-Exchange Chromatography on Mitsubishi Diaion UBA100S 1.00 mL of an aqueous mixture of gluconic acid (12 wt %) and glucaric acid (26 wt %) was injected into the HPLC system.

The following gradient elution conditions were employed:
1) flow rate 20 mL/min,
2) 1-50 min: 15 vol % acetic acid/85 vol % water,
3) 50.1-150 min: 50 vol % acetic acid/50 vol % water, and
4) fractions were collected and re-analyzed by HPLC.

Figure 3:
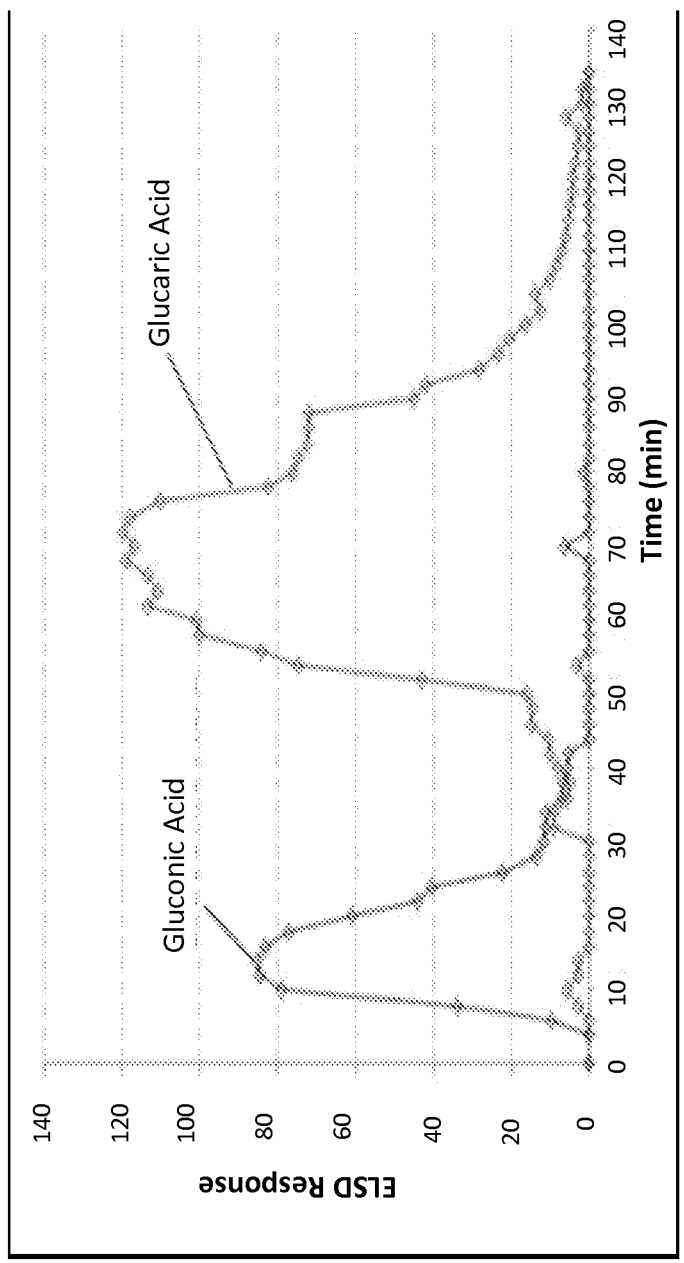
FIG. 3 depicts the separation of gluconic and glucaric acid by ion-exchange chromatography on a Mitsubishi Diaion UBA100S resin (Example 4).

The results are shown in FIG. 3. This result demonstrates that components of interest may be separated using ion exchange chromatography.

Example 5

Separation of Gluconic and Glucaric Acid by Ion-Exchange Chromatography on Mitsubishi Diaion UMA150

1.00 mL of an aqueous mixture of gluconic acid (12 wt %) and glucaric acid (26 wt %) was injected into the HPLC system.

The following gradient elution conditions were employed:
1) flow rate 20 mL/min,
2) 1-10 min: 10 vol % acetic acid/90 vol % water,
3) 10.1-90 min: 50 vol % acetic acid/50 vol % water, and
4) fractions were collected and re-analyzed by HPLC.

Figure 4:
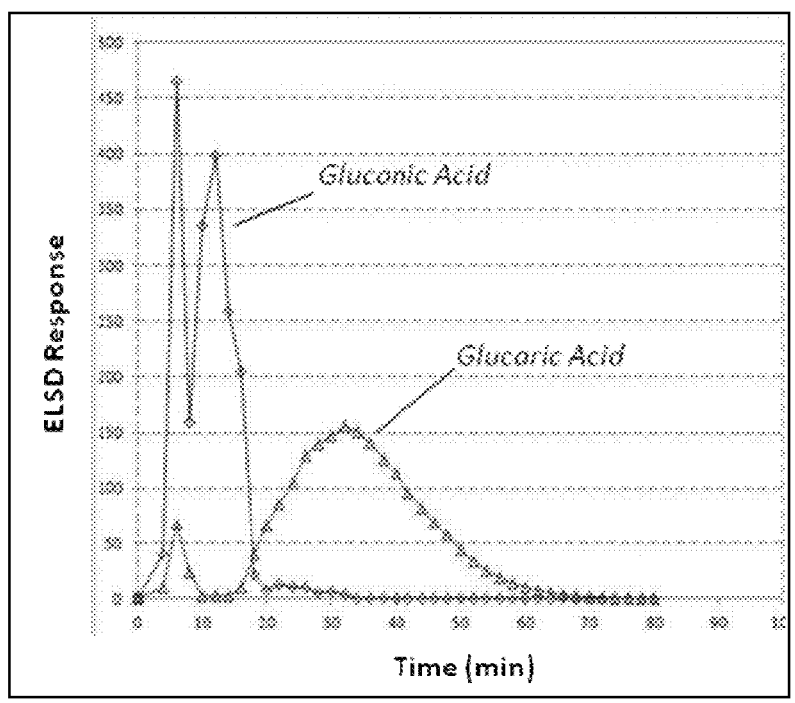
FIG. 4 depicts the separation of gluconic and glucaric acid by ion-exchange chromatography on a Mitsubishi Diaion UMA150 resin (Example 5).

The results are shown in FIG. 4. This result demonstrates that components of interest may be separated using ion exchange chromatography.

Example 6

Capture of Glucaric Acid Equilibrium Mixture and Release of Glucarolactones

Figure 5:
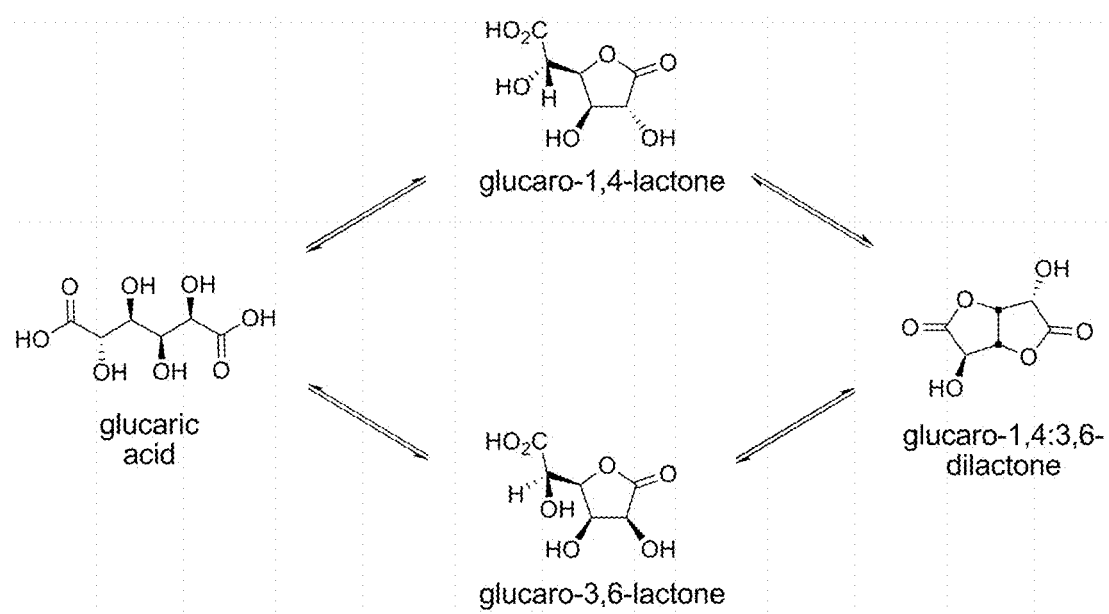
FIG. 5 depicts the aqueous phase equilibria between glucaric acid and glucarolactones.

In aqueous solutions of glucaric acid, equilibria are known to exist between acyclic glucaric acid, two distinct monolactones, and a dilactone. The equilibria that are known to exist are illustrated in FIG. 5. An aqueous solution of glucaric acid (1 ml of 200 mg/ml solution) was injected into the HPLC loaded with Mitsubishi Diaion UBA100S resin and eluted using the following gradient elution conditions:
1) flow rate 5 mL/min,
2) gradient elution:
   a) 2 minutes at 5 vol % acetic acid in water,
   b) 6 minute ramp from 5-95 vol % acetic acid in water,
   c) 1 minute ramp from 95-5 vol % acetic acid in water, and
   d) 10 minutes at 5 vol % acetic acid in water.

Fractions 1 and 2 were analyzed using an Agilent LC fitted with a hypercarb column connected to a Corona CAD detector. The separation was conducted at 45° C. using the following gradient elution conditions:
1) flow rate 1.2 mL/min,
2) gradient elution:
   a) 1 minute at 0.1 vol % formic acid in water,
   b) 7 minute ramp to 60 vol % water and 40 vol % of a solution containing (50 vol % MeOH/49.9 vol % water/0.1 vol % formic acid), and
   c) 9 minute ramp to 0.1 vol % formic acid in water.

The LC traces for Fractions 1 and 2 contained a mixture of 1,4 and 3,6-monolactones of glucaric acid only. No evidence for the presence of acyclic glucaric acid could be detected by LC-CAD. Peaks were assigned by comparison with calibration standards.

What is claimed is:

1. A process for the production of an adipic acid product, the process comprising the steps of oxidizing glucose to produce a mixture comprising at least one mono-carboxylic acid compound and at least one di-carboxylic acid compound, separating the at least one monocarboxylic acid compound in the mixture from the at least one di-carboxylic acid compound in the mixture, and converting at least a portion of the at least one di-carboxylic acid separated from the mixture to an adipic acid product, wherein separating the at least one monocarboxylic acid compound in the mixture from the at least one di-carboxylic acid compound in the mixture comprises the steps of:
   (a) contacting the mixture with an anion exchange chromatography medium to cause the at least one mono-carboxylic acid compound and the at least one di-carboxylic acid compound to be retained by the anion exchange chromatography medium;
   (b) eluting the at least one mono-carboxylic acid compound from the anion exchange chromatography medium using a first eluent to form a first eluate; and
   (c) eluting the at least one di-carboxylic acid compound from the anion exchange chromatography medium using a second eluent to form a second eluate;
   wherein the first eluate is enriched in the at least one mono-carboxylic acid compound retained by the medium relative to the concentration of such acid in the first eluent and comprises at least about 50 wt % of the at least one mono-carboxylic acid compound retained by the anion exchange chromatography medium, the second eluate is enriched in the at least one di-carboxylic acid compound retained by the medium relative to the concentration of such acid in the second eluent, and wherein the first eluent consists essentially of water or comprises from about 1 to about 20 vol % of an organic acid in water and the second eluent comprises an organic acid, and the concentration of the organic acid in the second eluent is greater than the concentration of the organic acid in the first eluent.

2. The process of claim 1, wherein the first eluent comprises the organic acid in water and the organic acid of each of the first eluent and second eluent has a pKa equal to or greater than about 3.7.

3. The process of claim 1, wherein the first eluent comprises the organic acid in water.

4. The process of claim 1, wherein each of the first eluent and the second eluent comprise acetic acid.

5. The process of claim 1, wherein the at least one mono-carboxylic acid compound is selected from the group consisting of C6 mono-carboxylic acid compounds and the at least one di-carboxylic acid compound is selected from the group consisting of C6 dicarboxylic acid compounds.

6. The process of claim 1, wherein the anion exchange chromatography medium is selected from the group consisting of a weak anion, tertiary amine anion exchange chromatography medium; a weak anion, secondary amine anion exchange chromatography medium; a strong anion, type I anion exchange chromatography medium; a strong anion, type II anion exchange chromatography medium; and a strong anion, type I with a weak acid anion exchange chromatography medium.

7. The process claim 1, wherein each of the first and second eluent comprise formic acid.

8. The process of claim 1, wherein the anion exchange chromatography is carried out using simulated moving bed (SMB) chromatography.

9. The process of claim 1, wherein the separation process is carried out at a temperature between 0° C. and 100° C.

10. The process of claim 4, wherein the second eluent comprises from about 40 to about 90 vol % acetic acid in water.

11. The process of claim 1, wherein the at least one mono-carboxylic acid compound retained by the medium is a compound of formula I:

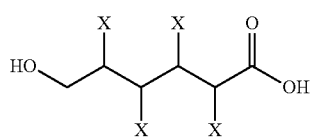

wherein each X is independently hydroxyl, oxo, acyloxy or hydrogen; and
the at least one di-carboxylic acid compound retained by the medium is a compound of formula II:

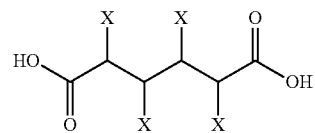

wherein each X is independently hydroxyl, oxo, acyloxy or hydrogen.

12. The process of claim 1, wherein the at least one mono-carboxylic acid compound retained by the medium is selected from the group consisting of gluconic acid, ketogluconic acids, glucuronic acid, and mixtures thereof.

13. The process of claim 1, wherein the at least one di-carboxylic acid compound retained by the medium is selected from the group consisting of C2-C6 di-carboxylic acid compounds.

14. The process of claim 1, wherein at least two di-carboxylic acid compounds are retained by the medium and such compounds are selected from the group consisting of C2, C4, and C6 di-carboxylic acid compounds and wherein at least one of such compounds is glucaric acid.

15. The process of claim 1, wherein the at least one mono-carboxylic acid compound retained by the medium comprises gluconic acid and the at least one di-carboxylic acid compound comprises glucaric acid.

16. The process of claim 1, wherein the first eluate comprises at least about 70 wt % of the at least one mono-carboxylic acid compound retained by the anion exchange chromatography medium and the second eluate comprises at least about 70 wt %, of the at least one di-carboxylic acid compound retained by the anion exchange chromatography medium.

17. The process of claim 1, wherein the at least one di-carboxylic acid compound comprises glucaric acid and at least one mono- or di-lactone, which are selected from the group consisting of glucaro-1,4-lactone, glucaro-1,4:3,6-dilactone, and glucaro-3,6-lactone.

18. The process of claim 1, wherein the at least one mono-carboxylic acid compound retained by the medium comprises gluconic acid, the at least one di-carboxylic acid compound comprises glucaric acid, and the adipic acid product comprises adipic acid.

19. The process of claim 18, wherein the first eluent is water.

20. A process for the production of a di-carboxylic acid compound, the process comprising the steps of oxidizing glucose to produce a mixture comprising at least one mono-carboxylic acid compound and the di-carboxylic acid compound, and separating the at least one monocarboxylic acid compound in the mixture from the di-carboxylic acid compound in the mixture, wherein separating the at least one monocarboxylic acid compound in the mixture from the di-carboxylic acid compound in the mixture comprises the steps of:
  (a) contacting the mixture with an anion exchange chromatography medium to cause the at least one mono-carboxylic acid compound and the di-carboxylic acid compound to be retained by the anion exchange chromatography medium;
  (b) eluting the at least one mono-carboxylic acid compound from the anion exchange chromatography medium using a first eluent to form a first eluate; and
  (c) eluting the di-carboxylic acid compound from the anion exchange chromatography medium using a second eluent to form a second eluate;

wherein the first eluate is enriched in the at least one mono-carboxylic acid compound retained by the medium relative to the concentration of such acid in the first eluent and comprises at least about 50 wt % of the at least one mono-carboxylic acid compound retained by the anion exchange chromatography medium, the second eluate is enriched in the di-carboxylic acid compound retained by the medium relative to the concentration of such acid in the second eluent, and wherein the first eluent consists essentially of water or comprises from about 1 to about 20 vol % of an organic acid in water and the second eluent comprises an organic acid, and the concentration of the organic acid in the second eluent is greater than the concentration of the organic acid in the first eluent.

21. The process of claim 20, wherein the first eluent is water.

22. The process of claim 20, wherein the first eluent comprises the organic acid in water.

23. The process of claim 20, wherein the first eluent comprises the organic acid in water and the organic acid of each of the first eluent and second eluent has a pKa equal to or greater than about 3.7.

24. The process of claim 20, wherein each of the first eluent and the second eluent comprise acetic acid.

25. The process of claim 20, wherein the second eluent comprises from about 40 to about 90 vol % acetic acid in water.

26. The process of claim 20, wherein the anion exchange chromatography medium is selected from the group consisting of a weak anion, tertiary amine anion exchange chromatography medium; a weak anion, secondary amine anion exchange chromatography medium; a strong anion, type I anion exchange chromatography medium; a strong anion, type II anion exchange chromatography medium; and a strong anion, type I with a weak acid anion exchange chromatography medium.

27. The process of claim 20, wherein the anion exchange chromatography is carried out using simulated moving bed (SMB) chromatography.

28. The process of claim 20, wherein the at least one mono-carboxylic acid compound is selected from the group consisting of C6 mono-carboxylic acid compounds and the at least one di-carboxylic acid compound is selected from the group consisting of C6 dicarboxylic acid compounds.

29. The process of claim 20, wherein the at least one mono-carboxylic acid compound retained by the medium is a compound of formula I:

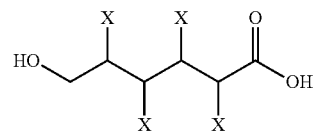

wherein each X is independently hydroxyl, oxo, acyloxy or hydrogen; and
the at least one di-carboxylic acid compound retained by the medium is a compound of formula II:

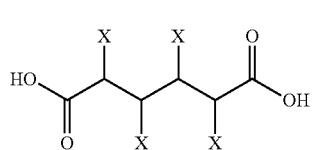

wherein each X is independently hydroxyl, oxo, acyloxy or hydrogen.

30. The process of claim 20, wherein the at least one mono-carboxylic acid compound retained by the medium is selected from the group consisting of gluconic acid, ketogluconic acids, glucuronic acid, and mixtures thereof.

31. The process of claim 20, wherein the at least one di-carboxylic acid compound retained by the medium is selected from the group consisting of C2-C6 di-carboxylic acid compounds.

32. The process of claim 20, wherein the at least one mono-carboxylic acid compound retained by the medium comprises gluconic acid and the at least one di-carboxylic acid compound comprises glucaric acid.

33. The process of claim 21, wherein the at least one mono-carboxylic acid compound retained by the medium comprises gluconic acid and the at least one di-carboxylic acid compound comprises glucaric acid.

34. The process of claim 20, wherein the first eluate comprises at least about 70 wt % of the at least one mono-carboxylic acid compound retained by the anion exchange chromatography medium and the second eluate comprises at least about 70 wt %, of the at least one di-carboxylic acid compound retained by the anion exchange chromatography medium.

* * * * *